United States Patent
Vogt et al.

(10) Patent No.: US 9,707,383 B2
(45) Date of Patent: Jul. 18, 2017

(54) URETERAL STENT AND METHOD FOR TREATING UROLOGICAL PROBLEMS

(71) Applicants: Benoit Vogt, Tours (FR); Francois-Noel Desfemmes, Autreche (FR); Arnaud Desgrippes, Blois (FR)

(72) Inventors: Benoit Vogt, Tours (FR); Francois-Noel Desfemmes, Autreche (FR); Arnaud Desgrippes, Blois (FR)

( * ) Notice: Subject to any disclaimer, the term of this patent is extended or adjusted under 35 U.S.C. 154(b) by 0 days.

(21) Appl. No.: 14/653,791

(22) PCT Filed: Dec. 19, 2013

(86) PCT No.: PCT/EP2013/077506
§ 371 (c)(1),
(2) Date: Jun. 18, 2015

(87) PCT Pub. No.: WO2014/096264
PCT Pub. Date: Jun. 26, 2014

(65) Prior Publication Data
US 2015/0343187 A1    Dec. 3, 2015

(30) Foreign Application Priority Data

Dec. 19, 2012  (FR) ..................................... 12 62293
Mar. 7, 2013   (FR) ..................................... 13 52061

(51) Int. Cl.
*A61M 27/00*    (2006.01)
*A61F 2/82*     (2013.01)

(52) U.S. Cl.
CPC ............. *A61M 27/008* (2013.01); *A61F 2/82* (2013.01)

(58) Field of Classification Search
CPC ............... A61F 2/04; A61F 2/06; A61F 2/008
(Continued)

(56) References Cited

U.S. PATENT DOCUMENTS

2012/0221117 A1* 8/2012 Chung ..................... A61F 2/04
                                                        623/23.66
2012/0303134 A1  11/2012 Amos, Jr.
(Continued)

FOREIGN PATENT DOCUMENTS

DE    3740288 C1    11/1987
DE    4103573 A1    2/1991
(Continued)

OTHER PUBLICATIONS

International Search Report dated Dec. 19, 2012 (Application No. PCT/EP2013/077506 (6 pages).
(Continued)

*Primary Examiner* — Suzette J Gherbi
(74) *Attorney, Agent, or Firm* — Blakely Sokoloff Taylor & Zafman LLP

(57) ABSTRACT

The proposed invention is a ureteral stent (2) comprising a kidney end part (200) and a bladder end part (210), the kidney end part (200) being tubular and curved, said stent (2) being characterized in that the bladder end part (210) has at least one thread, and in that the stent additionally comprises a tubular intermediate portion (220) extending between the kidney end part and the bladder end part, said portion having an external diameter decreasing towards the bladder end part, and the minimal external diameter of said portion (220), at the connection to the thread of the bladder end part (210), is substantially equal to the diameter of the thread, said portion having a length of between 0.5 cm and 12 cm.

25 Claims, 10 Drawing Sheets

(58) Field of Classification Search
USPC .............................................. 623/23.64–23.7
See application file for complete search history.

(56) References Cited

U.S. PATENT DOCUMENTS

| | | | | |
|---|---|---|---|---|
| 2013/0024003 | A1* | 1/2013 | McWeeney | A61M 27/008 623/23.69 |
| 2013/0297039 | A1* | 11/2013 | Lloyd | A61F 2/042 623/23.66 |
| 2014/0142721 | A1* | 5/2014 | Robertson | A61L 31/145 623/23.66 |
| 2015/0005893 | A1* | 1/2015 | Harrah | A61L 31/148 623/23.7 |
| 2015/0142127 | A1* | 5/2015 | Ponsky | A61M 27/008 623/23.69 |
| 2015/0150698 | A1* | 6/2015 | Ponsky | A61M 27/008 623/23.65 |
| 2015/0223953 | A1* | 8/2015 | Pendleton | A61F 2/852 623/23.68 |

FOREIGN PATENT DOCUMENTS

| | | |
|---|---|---|
| EP | 2308527 A1 | 4/2011 |
| WO | WO 2005/096991 A1 | 10/2005 |

OTHER PUBLICATIONS

Written Opinion dated Dec. 19, 2012 (Application No. PCT/EP2013/077506) (8 pages).
Preliminary Search Report dated Aug. 26, 2013 (Application No. FR 1352061) (10 pages).
Dauleh et al., Non refluxing minimal irritation stent in British Journal of Urology, 1995.
Kawahara et al., Changing to a loop-type ureteral stent decreases patients' stent-related symptoms, in Urol Res (2012) 40 : 763-767.
Lingeman et al., Assessing the Impact of Ureteral Stent Design on Patient Comfort, in J. Urol. Jun. 2009; 181(6): 2581-2587.
A brochure by Boston Scientific dated 2010—"Percuflex".
A brochure by Boston Scientific dated 2006—"Polaris Loop".
Yves Ponsot et al., Simple Modification of the Double J Stent to Improve its Clinical Acceptability, in Progres en Urologie, 1994, 4, 420-422.

* cited by examiner

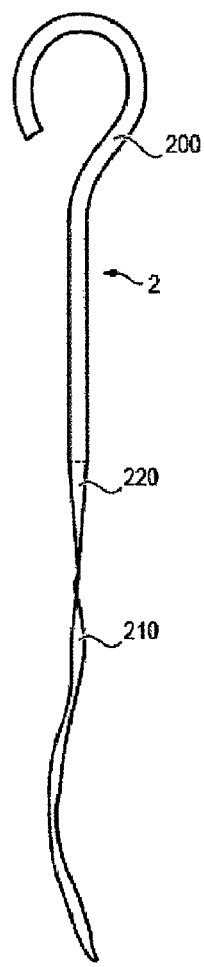
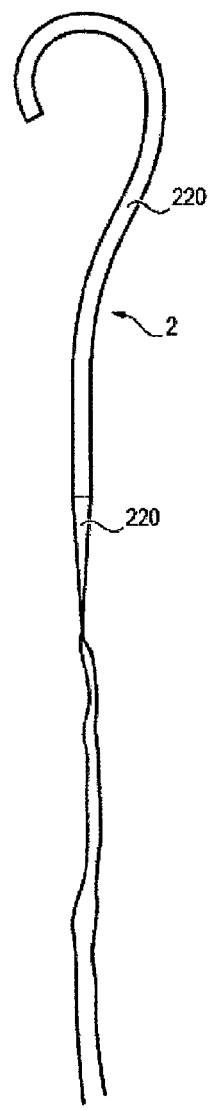

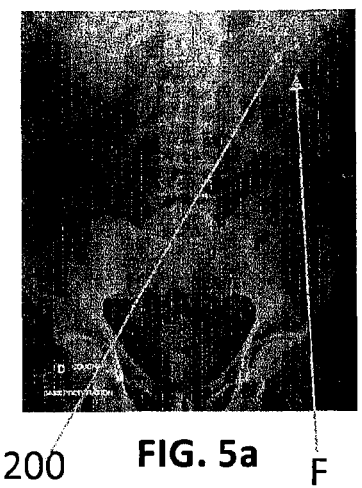 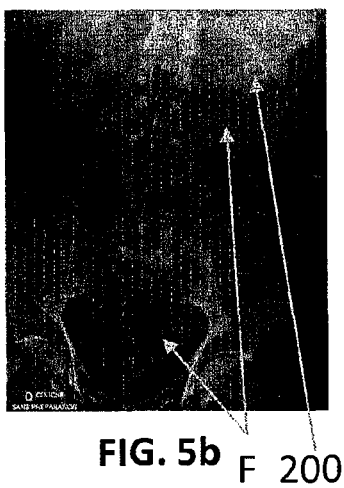 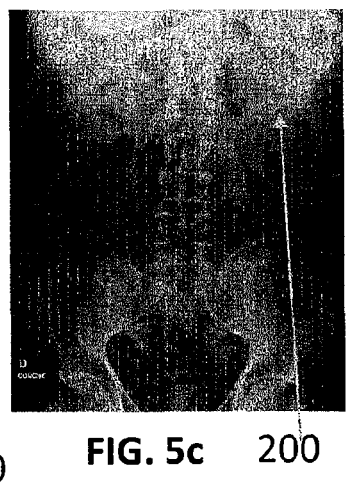
200  FIG. 5a  F          FIG. 5b  F  200          FIG. 5c  200

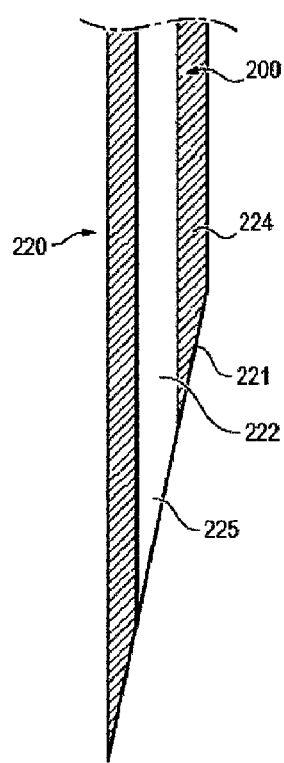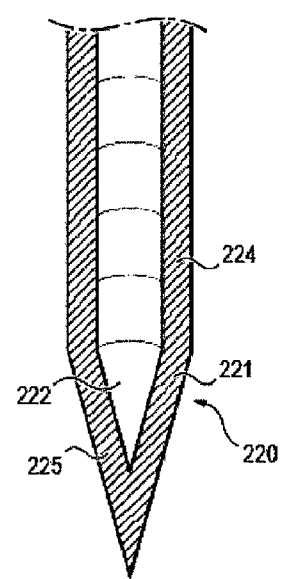
FIG. 6a
FIG. 6b

URETERAL STENT AND METHOD FOR TREATING UROLOGICAL PROBLEMS

FIELD OF THE INVENTION

The field of the invention is that of endo-ureteral stents, used for maintaining the flow of urine in the ureter.

PRIOR ART

With reference to FIG. 1, the ureter U is a channel connecting a kidney R to the bladder V, and wherein urine flows freely in the absence of obstacles.

The ureter can become obstructed in some conditions, for example in the presence of kidney stones C, pyeloureteral junction syndromes, in cases of extrinsic compression by malignant or benign retroperitoneal fibrosis, in cases of ureteral or pyelic tumour, or again in cases of ischaemic or post-radiation ureteral stenosis.

In cases of obstruction of the ureter, the urine no longer manages to flow to the bladder and the kidney dilates. An attack of renal colic then occurs.

To remedy this obstruction, it is known to use a tubular endo-ureteral stent 1, having a median portion 10 placed in the ureter, this portion extending between two ends 12, 14.

A first end 12 opens in the kidney, and a second end 14 opens in the bladder, these two ends being coiled to ensure the stent is held in position. Due to these ends being coiled into a J shape, such a stent is commonly called a "JJ stent".

JJ stents are generally made of polyurethane, silicone or metal and have an average diameter of 6 or French, i.e. 2 or 2.3 mm. They are put in for a period of 6 to 12 months.

The stent 1 comprises over its whole length a plurality of through holes 16, allowing communication of the fluid, in this case urine, between the internal channel of the stent and the environment in which it is placed.

After placing the stent, the urine can thus flow freely again between the kidney and the bladder through the stent 1 and the holes 16. It can only flow via the internal channel of the stent or between the walls of the stent and the ureter, depending on the nature and position of the obstacle in the ureter.

JJ stents have already proved very useful, but they nonetheless have some drawbacks.

Firstly, after this stent is put in, the urine can not only flow freely from the kidney to the bladder, but also in the reverse direction from the bladder to the kidney, because the stent opens an anatomical system that normally prevents the urine from flowing back from the bladder to the kidney.

This abnormal reflux of urine to the kidney is unpleasant and painful.

Furthermore, due to its diameter this stent can rub inside the bladder or against the ureter, and give irritation, oedemas, pelvic congestion, or else an overwhelming need to micturate in both men and women.

For all these reasons, the stent is poorly tolerated by around 80% of patients.

To remedy this unpleasantness, in the document EP2308527 an endo-ureteral stent has been proposed, the bladder end J-shaped part of which is replaced by at least two threads connected at their ends in such a way as to form loops of thread. Each thread has a diameter above 0.5 French, i.e. above 0.16 mm, preferably between 2 and 4 French, i.e. between 0.66 and 1.3 mm, so as to obtain, with both curved threads, a large enough section to allow good drainage of the urine. The rod is also described as being generally rigid to retain the memory of the shape.

This is because it is considered imperative to preserve a thick enough thread to allow drainage of the urine, in order to avoid the risk of not draining the urine and causing obstructive pyelonephritis, or even iatrogenic septic shock.

For these reasons, the stent proposed by this document does not solve the problems described above because it still gives rise to irritation.

PRESENTATION OF THE INVENTION

The aim of the invention is to palliate the problems mentioned above. In particular, the aim of the invention is to propose an endo-ureteral stent allowing drainage of the urine from the kidney to the bladder, without giving rise to irritation or reflux in the patient.

In this regard, the subject of the invention is an endo-ureteral stent, comprising a kidney end part and a bladder end part, the kidney end part being tubular and coiled, said stent being characterized in that the bladder end part includes at least one thread, and in that the stent further comprises a tubular intermediate portion extending between the kidney end part and the bladder end part, said portion having an external diameter decreasing toward the bladder end part, and the minimum external diameter of the tubular intermediate portion, at the point of connection with the bladder end portion, is equal to the diameter of the thread(s) of the bladder end part, said intermediate portion having a length between 0.5 cm and 12 cm.

Advantageously, but optionally, the stent according to the invention can further comprise at least one of the following features:

- the thread(s) is/are of circular section, each thread having a diameter of less than 0.15 mm.
- The bladder end part includes a single thread.
- The intermediate portion has a length of 3 cm.
- The diameter of the intermediate portion decreases evenly over the whole length of said portion.
- The intermediate portion is bevelled.
- The bevelled intermediate portion comprises a tubular portion and a solid portion ending said portion, the bladder end part comprising a thread crossing the wall of the solid portion and the wall of the tubular portion or of the kidney end part.
- The intermediate portion comprises a tubular portion and a solid portion extended by the bladder end portion, the thread of the bladder end portion being formed on a wall of the intermediate portion. The bladder end part has a length greater than or equal to 2 cm, preferably between 5 and 30 cm.
- The kidney end part and the intermediate part each comprise a plurality of through perforations.
- The stent further comprises a tubular ureteral portion arranged between the kidney end part and the intermediate portion, said ureteral portion having an external diameter equal to that of the kidney end part and being unperforated.
- The tubular ureteral portion has a length between 10 and 25 cm.

Another subject of the invention is a method for treating a urological disorder by implanting an endo-ureteral stent, the method comprising:

- implanting an endo-ureteral stent in the ureter of the subject, the endo-ureteral stent comprising a kidney end portion, a bladder end portion, and an intermediate portion extending between the kidney end portion and the bladder end portion, the intermediate portion having an external diameter decreasing toward the bladder end portion, and the bladder end portion comprising at least one thread extending from the intermediate portion, and treating a urological disorder by dilating the ureter with the endo-ureteral stent.

In certain embodiments, the method for treating a urological problem can further comprise at least one of the following features:

implanting the stent comprises positioning the kidney end portion in a kidney of the subject and at least one thread in the ureter so that said at least one thread causes dilation of the ureter.

Implanting the stent comprises positioning the kidney end portion in the kidney and the intermediate portion in the ureter so that said at least one thread extends from the ureter into the bladder.

Implanting comprises positioning the intermediate portion in the kidney so that said at least one thread extends from the kidney into the bladder.

The urological disorder comprises kidney or ureteral stones, and the dilation of the ureter comprises the dilation of the ureter with said at least one thread having a diameter that allows stones, or fragments of said stones, to be evacuated naturally during urination.

The urological disorder comprises one of kidney stones, ureter stones, obstructive syndrome of the pyeloureteral junction, extrinsic ureteral tumor stenosis, malignant retroperitoneal fibrosis, benign retroperitoneal fibrosis, ischaemic ureteral stenosis, post-radiation ureteral stenosis or intrinsic tumoral ureteral or pyelic stenosis.

Another subject of the invention is a method of treating a urological disorder by implanting an endo-ureteral stent, the method comprising:

implanting an endo-ureteral stent within a ureter of a subject, the endo-ureteral stent having a thread portion of a suitable size to dilate the ureter, and treating a urological disorder by dilating the ureter with the thread portion of the endo-ureteral stent.

In certain embodiments, this treatment method further comprises at least one of the following features:

The thread portion comprises a circular section having a diameter of less than 0.15 mm.

The endo-ureteral stent further comprises a tubular portion having a decreasing diameter toward a first end until the diameter of the thread portion, and wherein the thread portion extends from said end of the tubular portion, and implanting comprises positioning the tubular portion in a kidney of the subject and the thread portion in the ureter.

The tubular portion comprises a coiled portion at an end opposite the first end, and the coiled portion and the first end have holes, and a ureteral portion between the coiled portion and the first end is without holes, and implanting comprises positioning the ureteral portion and the thread portion in the ureter.

The urological disorder comprises kidney stones or ureteral stones, and treating comprises evacuating the stones, or fragments of the stones, from the kidney or ureter while the endo-ureteral stent remains implanted in the ureter.

The urological disorder comprises one of kidney stones, ureter stones or obstructive syndrome of the pyeloureteral junction and implanting comprises positioning a tubular portion of the endo-ureteral stent in a kidney of the subject and the thread portion in the ureter.

The urological disorder comprises one of an extrinsic ureteral tumor stenosis, malignant retroperitoneal fibrosis, benign retroperitoneal fibrosis, ischaemic ureteral stenosis, post-radiation ureteral stenosis or intrinsic tumoral ureteral or pyelic stenosis.

Surprisingly, and counter to established prejudice among practitioners, the small diameter of the bladder end part is sufficient to allow drainage of the urine into the bladder. Additionally, this part gives little or no irritation or discomfort in the patient in whom the stent has been implanted.

Even more surprisingly, it has been observed that placing such a stent gives rise to dilation of the meatus and the ureter by the thread of the bladder end part. This dilation of the meatus allows easy introduction of a rigid ureteroscope (of a diameter in the order of 4 to 5 mm) or of a flexible ureteroscopy sheath, of a diameter in the order of 3 to 4 mm, into the ureter.

Furthermore, the stone fragments are evacuated around the thread(s) and the kidney end part without any nephritic colic pain. This phenomenon is explained by the fact that the dilation of the ureter promotes the evacuation of fragments, and the thread(s) prevent gross obstructions.

Lastly, as the intermediate portion of decreasing diameter between the two end parts is evenly tapered, it reduces the risk of oedema that may result from the stent catching in a portion of the ureter.

OVERVIEW OF THE FIGURES

Other features, aims and advantages of the invention will become apparent on reading the following description, which is purely illustrative and non-limiting, and which must be read with reference to the appended drawings wherein:

FIG. 1, already described, schematically represents the implanting of a stent of the prior art in a ureter containing a kidney stone.

FIG. 2a schematically represents an endo-ureteral stent in accordance with an embodiment of the invention, FIG. 2b schematically represents the implanting of a stent represented in FIG. 2a in a ureter containing a ureteral stone.

FIGS. 2c and 2d represent two variants of the stone of FIG. 2a.

FIG. 3a schematically represents an endo-ureteral stent in accordance with the second embodiment of the invention.

FIG. 3b schematically represents the implanting of a stent from FIG. 3a in a ureter.

FIGS. 5a to 5c are X-ray photographs representing the natural evacuation of a stone following the placing of a stent.

FIGS. 6a and 6b represent longitudinal cutaway views of an intermediate portion of a stent.

Figure 7A:
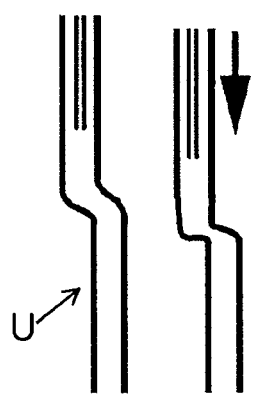
Figure 7B:
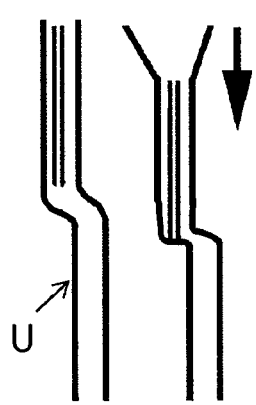
Figure 7C:
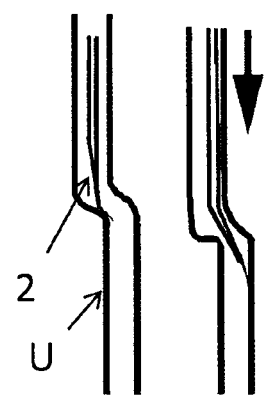

FIGS. 7a to 7c schematically illustrate the movement of a stent when a person breathes.

Figure 1:
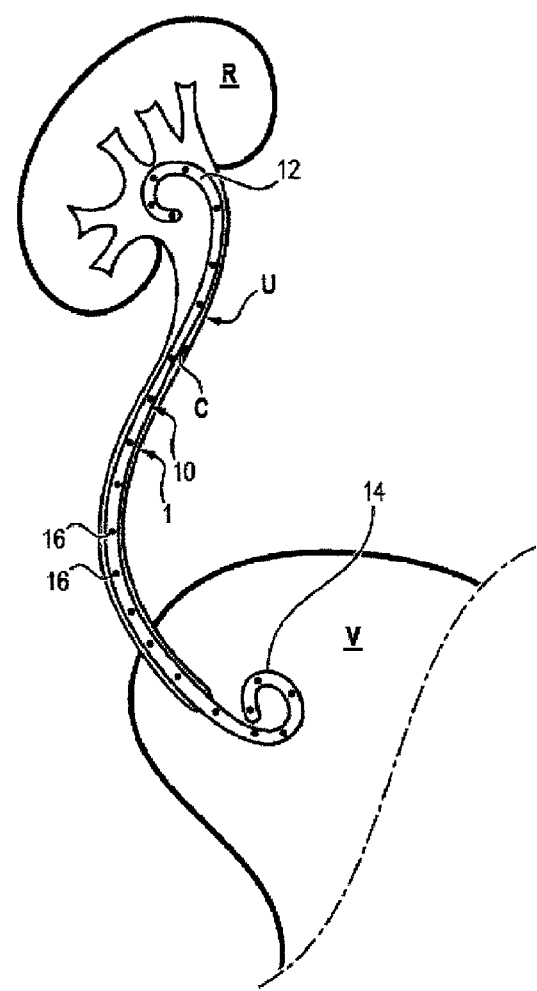
Figure 2A:
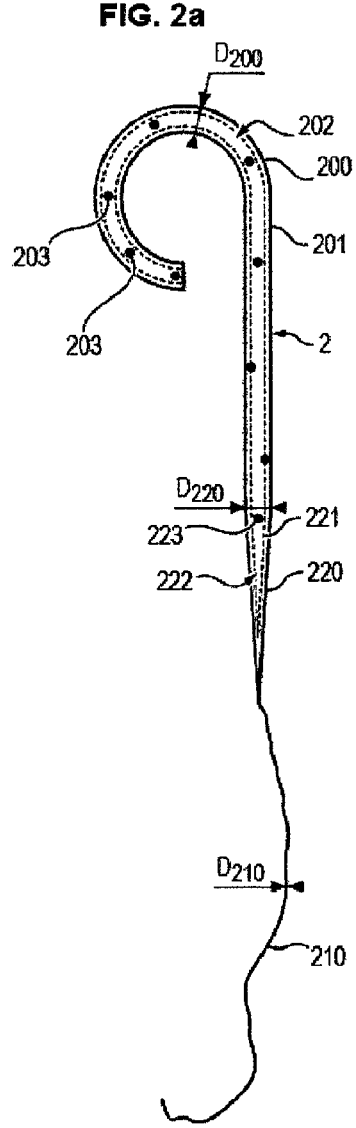
Figure 8A:
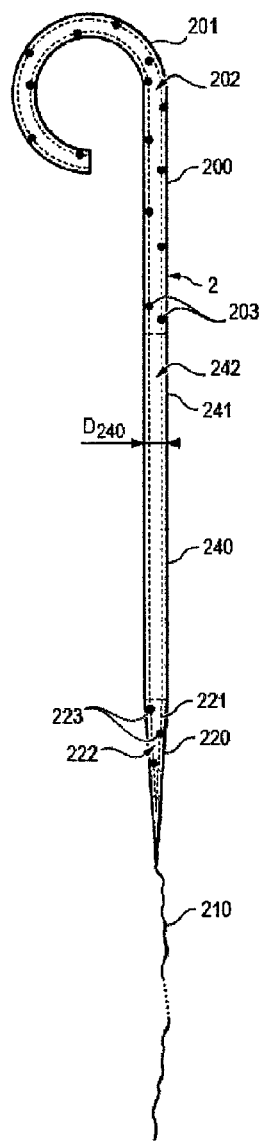

FIG. 8a schematically represents an endo-ureteral stent according to a variant embodiment of that in FIG. 2a.

Figure 8B:
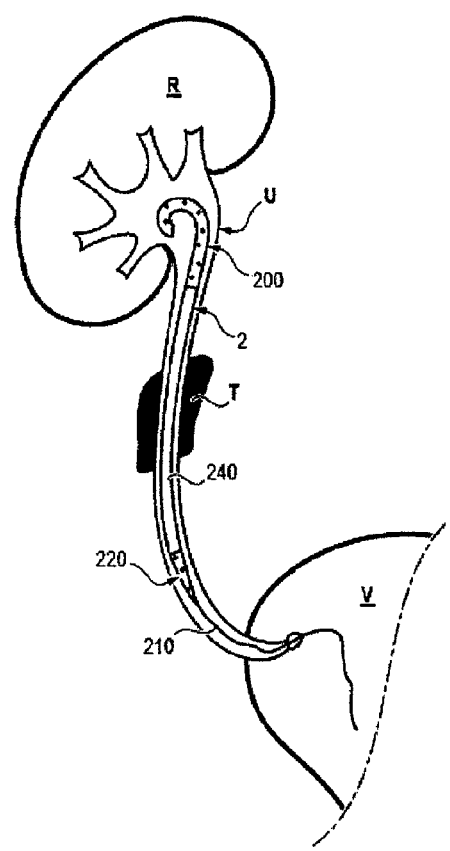

FIG. 8b schematically represents the implanting of the stent from FIG. 8a in a ureter compressed by an extrinsic tumor.

Figure 9A:
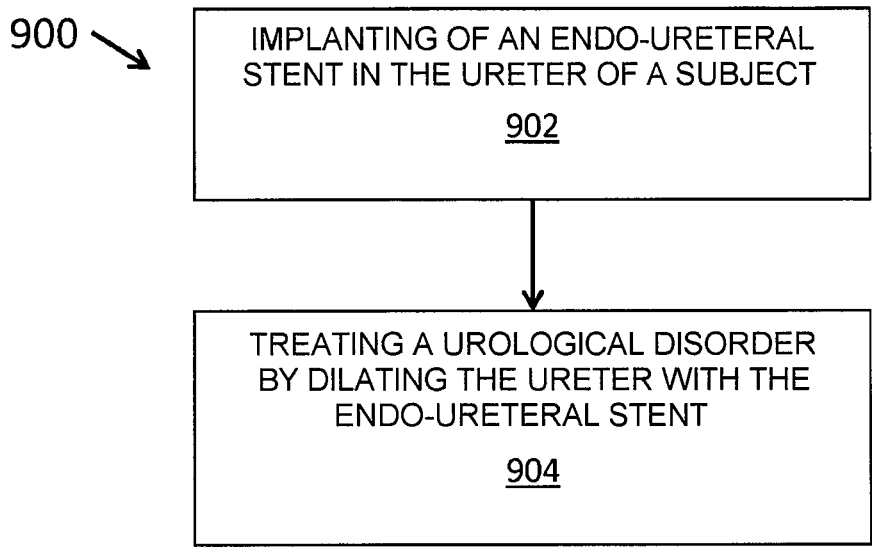
Figure 9B:
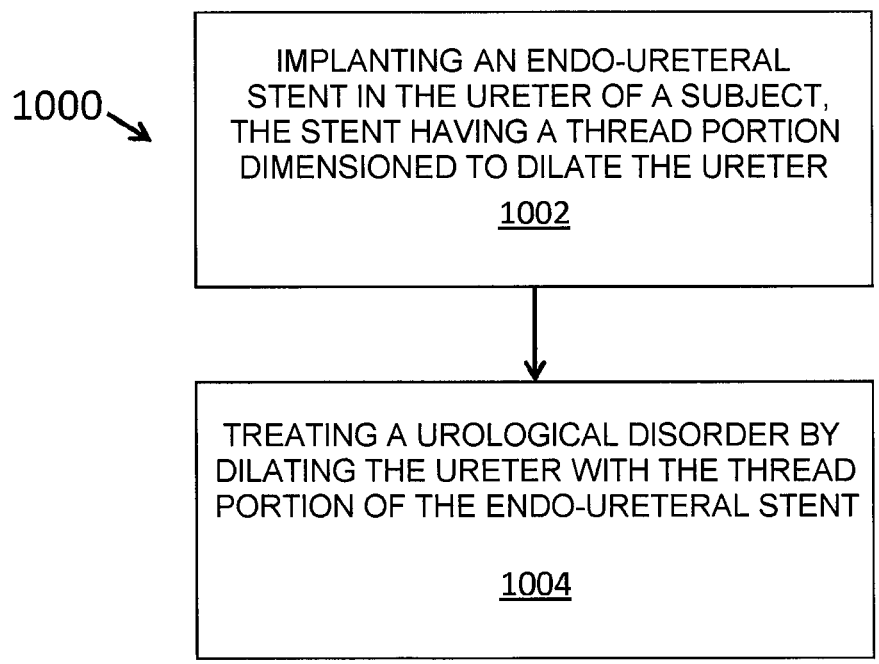

FIGS. 9a and 9b schematically represent the steps of a therapeutic treatment employed using the stent.

DETAILED DESCRIPTION OF AT LEAST ONE EMBODIMENT OF THE INVENTION

With reference to FIG. 2a, an embodiment of an endo-ureteral stent is represented.

This stent 2 includes a first kidney end part 200. This part is tubular, i.e. it comprises a cylindrical wall 201 delimiting an internal channel 202 wherein a fluid can circulate. A plurality of through holes 203 are further arranged in the cylindrical wall 201, allowing the fluid to enter into the internal channel 202 or exit it via the wall 201.

The kidney end part 200 is coiled into a J shape, i.e. it has a semi-circular or loop-shaped end (i.e. in the shape of a ring) allowing this part 200 to be held inside a kidney R once the stent is implanted.

Alternatively, this part can have one or more segments linked together by rounded bends to avoid any abrupt or cutting section.

Figure 2B:
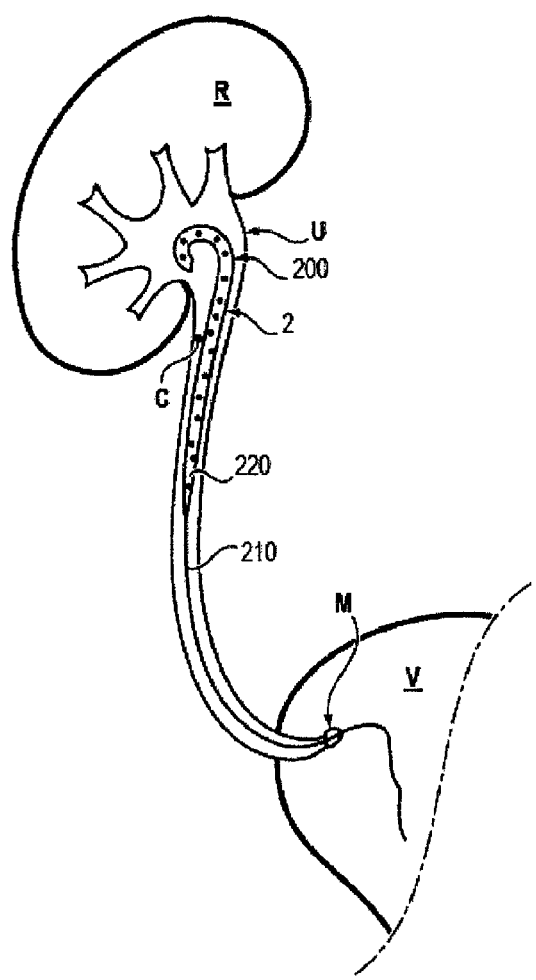

With reference to FIG. 2b, the kidney end part 200 is configured to enter the kidney once the stent is in place, and extend from the kidney R to the ureter U of the patient. In this regard, it has a length, when coiled, between 6 and 20 cm, preferably between 8 and 10 cm, advantageously equal to 9 cm. This corresponds to a total length, when this part is kept straight, between 12 and 26 cm, preferably between 14 and 16 cm, and advantageously in the order of 15 cm. This variation in length depends on the location of the obstacle in the ureter, specifically because the kidney end part 200 advantageously "by-passes" the obstacle, i.e. it ends at a place in the ureter where there is no longer an obstacle.

Figure 3A:
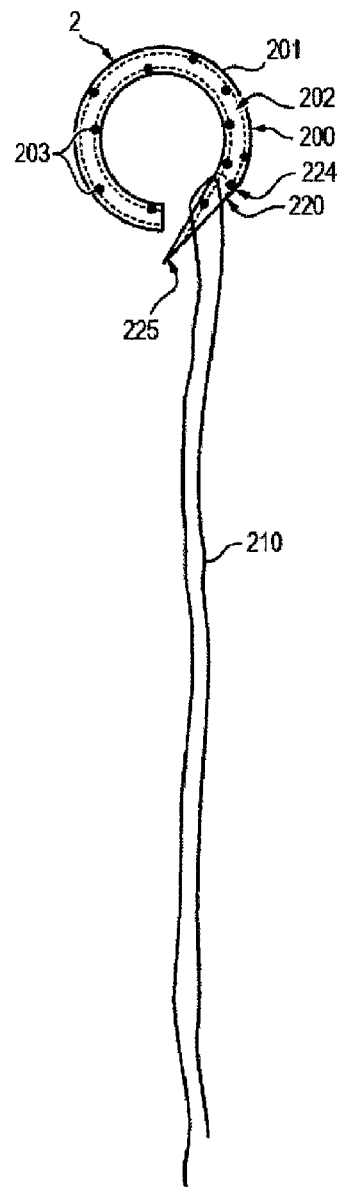
Figure 3B:
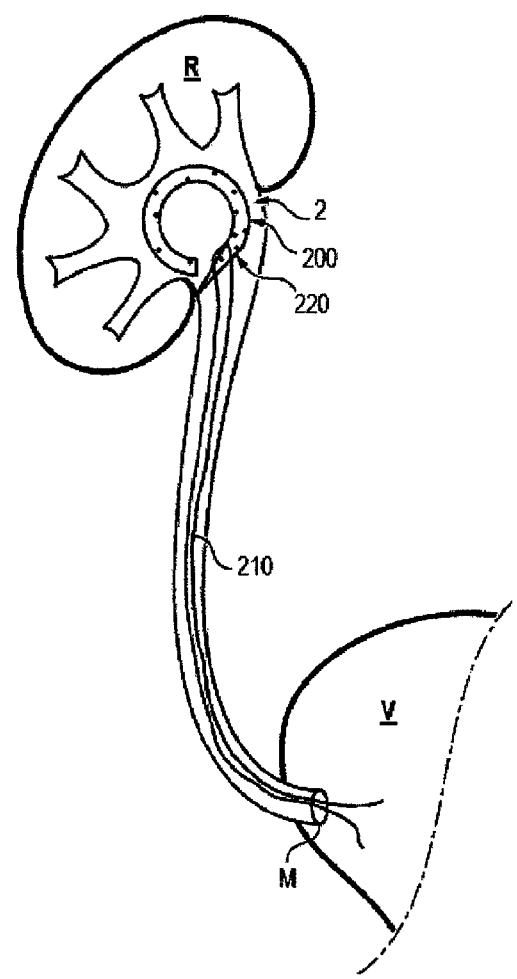

In a variant embodiment represented in FIGS. 3a and 3b, this kidney end part is limited to the loop of the "J", i.e. to a single tubular ring, in the order of 22 mm in diameter when the loop is coiled, which corresponds to a length, when this part is kept straight, in the order of 7 cm, or more generally a diameter between 10 and 25 mm, the minimum diameter serving to prevent the loop from entering the ureter in a coiled state, and the maximum useful diameter being limited to avoid causing pain or inconvenience.

Going back to the embodiment in FIG. 2a, the part 200 has a constant external diameter $D_{201}$, between 2 and 3.4 mm (or 6 to 10 French), preferably between 2 and 2.4 mm (or 6 to 7 French), and very advantageously in the order of 2.4 mm (or 7 French). On the other hand, in the embodiment in FIGS. 3a and 3b, this part 200 preferably has a constant external diameter between 1 and 3 mm, preferably in the order of 2 mm (or 6 French), or of 1.6 mm (or 4.8 French) so that this shorter part is also more flexible to allow it to unfold upon removal.

In the two embodiments in FIGS. 2a, 2b and 3a and 3b, the stent 2 further has a second bladder end part 210, intended to enter the bladder V, and extend from the ureter U into the bladder V. This part comprises at least one thread, and can preferably comprise a single thread, which can be free or folded to form a loop, as illustrated in FIG. 2c, or two threads, illustrated in FIG. 2d, preferably solid, i.e. of a circular section and without an internal channel. The absence of internal channel removes the risk of reflux of the urine to the kidney.

With reference to FIG. 2b, each thread has a constant external diameter $D_{210}$, of less than 0.15 mm (or 0.45 French), preferably between 0.05 and 0.15 mm, even more advantageously between 0.1 and 0.15 mm, i.e. 0.3 to 0.45 French), and preferably equal to 0.1 mm or 0.3 French. In all cases, the diameter of the thread or the cumulative section of the threads must not exceed 0.3 mm.

Although the use of a single thread is sufficient to drain the urine, the use of a loop of threads can be more reassuring in the event of one of the two breaking.

Separation into two threads also avoids the rigidity of a single, thicker wire.

The inventors have discovered that, surprisingly, the use of a single thread of small diameter makes it possible to drain the urine from the ureter to the bladder, contrary to widespread prejudice in the field.

This is because, surprisingly, the proposed stent, and in particular the small-diameter thread, lead to a dilation of the ureter, within a time period of two weeks to ten days after the stent is put in.

Even more surprisingly, putting in a stent, and particularly a stent in accordance with the embodiment in FIGS. 3a and 3b, i.e. when the kidney end portion of the stent is limited to a loop arranged in the kidney, also leads, in around 50% of cases, to dilation of the renal cavities (pelvis and calyces). These dilations do not lead to any pain.

Figure 4A:
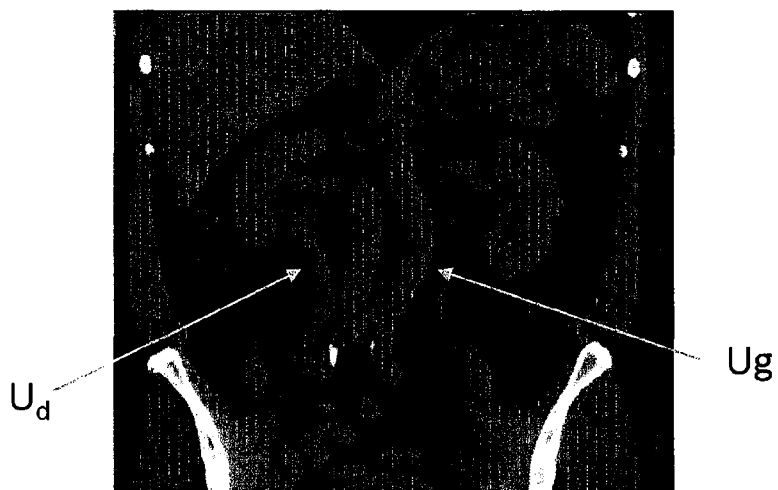
FIG. 4a is a scan performed on a patient in whom a stent has been placed, illustrating the dilation of the ureter following the placing of the stent.

The dilation of the ureter can be seen in FIG. 4a, which is a scan of a patient in whom a stent has been placed in the right ureter, the other ureter being without a stent. The right ureter Ud, on the left in the figure, appears highly dilated, particularly by comparison with the left ureter Ug on the right.

Figure 4B:
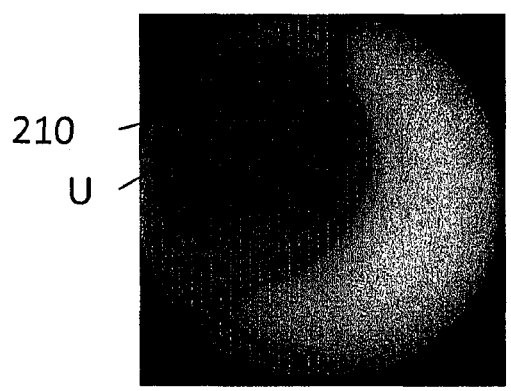
FIG. 4b is a photograph of the inside of the ureter with a stent placed therein, and which also illustrates the dilation of the ureter.

The dilation of the ureter can also be seen in FIG. 4b, which is a photograph of the inside of the ureter taken during an endoscopy. Note the thread 210 of the stent.

Statistical measurements of the dilation of the ureter have been taken on patients containing only one stent, comparing the diameters of the ureter and the renal pelvis on the side with the stent to the same diameters on the stentless side.

Stent S1 is a stent in accordance with the embodiment in FIGS. 2a and 2b, and Stent S2 is a stent in accordance with the embodiment in FIGS. 3a and 3b, wherein the kidney part is shorter and the intermediate portion 220 is also in the kidney.

The results of the diameter measurements are represented in Table 1.

TABLE 1

|  | Stent S1 side | Contralateral side | p | Stent S2 side | Contralateral side | p |
| --- | --- | --- | --- | --- | --- | --- |
| Number of scans analyzed | 17 |  |  | 13 |  |  |
| Interval between placing and scan (days) | 43.4 ± 34.1 |  |  | 49.4 ± 22 |  |  |
| Dilation of the cavities | 31.3% |  |  | 50.0% |  |  |
| Pelvis (mm) | 17.8 ± 4.9 | 5.1 ± 1.4 | 0.003 | 17.4 ± 8.3 | 7.8 ± 4.7 | 0.003 |

TABLE 1-continued

|  | Stent S1 side | Contralateral side | p | Stent S2 side | Contralateral side | p |
|---|---|---|---|---|---|---|
| Lumbar ureter (mm) | 8.7 ± 1.7 | 3.1 ± 0.5 | 0.00000001 | 9.7 ± 2.9 | 4.2 ± 1.6 | 0.00005 |
| Iliac ureter (mm) | 6.5 ± 1.3 |  | 0.000006 | 8.1 ± 1.6 | 3.2 ± 0.9 | 0.000001 |
| Pelvic ureter (mm) | 6.5 ± 1.4 | 3.8 ± 0.8 | 0.000001 | 6.4 ± 2.0 | 3.3 ± 0.8 | 0.0004 |

Such a dilation provokes another unforeseen effect: that of the natural evacuation of fragments of stones present in the kidney or in the ureter.

This applies in the case of fragments of stones (or whole stones) sliding without oedema into a healthy ureter.

Consequently, a method of treating kidney stones is proposed. A first step consists in implanting a stent in the ureter and the kidney. If a stone is present without leading to any obstruction of the ureter, the stent used is preferably in accordance with the embodiment in FIGS. 3a and 3b, because it is not necessary to drain the urine via the inside of the stent to circumvent an obstacle.

Alternatively, if there is an obstruction in the ureter, it is possible to use a stent, the intermediate portion of which is found in the ureter in accordance with the embodiment in FIGS. 2a and 2b, to drain the urine beyond the obstacle via the inside of the stent.

After the stent is put in, the ureter is dilated over its whole length, and in addition the thread(s) of the stent are thin enough not to encumber the ureter, and allow for the insertion of a urethroscope associated with an ad hoc tool, for example a laser fiber, to treat a stone locally. It is therefore not necessary, unlike operations previously conducted after placing a JJ stent, to remove the JJ stent to treat the stone, then to put the stent back in place. This results in a reduction of the number of manipulations in, and cost of the operation.

After the stent is put in, treatment then differs according to the size of the stone to be evacuated. For small stones, of a size below around 10 mm, these stones can be evacuated naturally from the ureter to the bladder by the flow of urine into the ureter, then from the bladder to the outside by urination.

In the case of stones of larger size, for example above 10 mm, a second step consists in breaking the stone into fragments.

This step is preferably employed some time after the placing of the stent, so that the ureter is sufficiently dilated. Thus it is preferable to wait for an interval of ten days after placing the stent, and preferably in the order of fifteen days to three weeks to break the stone into fragments.

This fragmentation can be carried out using known methods by extracorporeal lithotripsy, or by ureteroscopy (shock waves or laser) or by percutaneous nephroscopy (shock waves or laser).

The stones or fragments then slide from the kidney to the ureter, then from the ureter into the bladder and finally out of the bladder without pain.

FIGS. 5a to 5c are X-ray photographs from a patient at different stages of evacuation of kidney stone fragments. On the day the X-ray photograph in FIG. 5a was taken, a stent 2 in accordance with the embodiment in FIGS. 3a and 3b had been positioned in the ureter 15 days beforehand, and the stone was divided into fragments F.

The X-ray photograph in FIG. 5b was taken thirty days after placing the stent, and in it the motion of the fragments F can be observed.

The X-ray photograph in FIG. 5c was taken 42 days after placing the stent, and it was noted that all the fragments had been evacuated.

The inventors reported that the observed dilations disappear after removing the stent.

Furthermore, due to its limited diameter, the thread is very flexible and does not cause any irritation, so the patients are relieved and experience an improvement in their well-being.

Finally, and unlike previously used stents, which were systematically calcified, the inventors noted with surprise that no calcification appears in the thread(s) 210 until at least six months after putting in the stent.

The reduction in the inconvenience following the placing of a stent has been quantified in a group of patients. This improvement concerns the bladder tolerance and is certainly due to the extreme thinness of the thread 210.

Table 2 summarizes the urinary symptoms experienced by patients in whom a poorly tolerated JJ stent was replaced by a Stent S1 (FIGS. 2a and 2b). The tolerance of the thread 210 compared with respect to the tolerance of the bladder part of the JJ stent was evaluated by questionnaire.

Each question presented five possible answers, to which scores of 1 to 5 were assigned, 1 being the score assigned to the answer corresponding to zero inconvenience and 5 to the worst discomfort.

For example, for a question relating to the frequency of urine leaks, the score 1 is attributed to the answer "Never", 2 to the answer "Rarely", 3 to "Sometimes", 4 to "Most of the time", and 5 to "All the time".

Table 2 indicates the average scores experienced by the patients.

TABLE 2

| Group of patients (N = 24) | | | |
|---|---|---|---|
| Urinary symptoms | JJ stent | Stent S1 after JJ | p |
| Pollakiuria | 3.7 ± 1.3 | 2.8 ± 1.1 | 0.005 |
| Nycturia | 3.8 ± 1.1 | 2.8 ± 1.2 | 0.0001 |
| Urgency | 3.2 ± 1.2 | 2.4 ± 1.0 | 0.01 |
| Urgency not held in | 2.0 ± 0.9 | 1.8 ± 0.8 | 0.46 |
| Non-urgent incontinence | 1.8 ± 0.9 | 1.1 ± 0.3 | 0.004 |
| Feeling of residue | 3.0 ± 1.2 | 1.8 ± 0.9 | 0.00003 |
| Ureteral burning | 3.9 ± 1.3 | 1.8 ± 1.1 | 0.00000005 |
| Haematuria | 2.8 ± 1.4 | 1.6 ± 0.8 | 0.0006 |
| Appearance of the urine | 2.1 ± 0.8 | 1.6 ± 0.8 | 0.01 |
| Social impact | 3.8 ± 1.0 | 2.3 ± 0.9 | 0.00003 |
| Impact on quality of life | 5.3 ± 2.0 | 3.8 ± 1.6 | 0.0007 |
| Total score | 35.2 ± 7.5 | 23.6. ± 5.4 | 0.000002 |

Going back to FIG. 2a, the bladder end part 210 has a length greater than or equal to 2 cm, preferably between 5 and 30 cm, preferably between 20 cm and 28 cm.

In this regard, if the bladder end part is composed of a folded thread, for example folded at its middle, to form a double thread, the thread used therefore measures the double of the bladder end part, i.e. at least 4 cm, and preferably between 10 and 60 cm.

The part of the thread entering into the bladder V after placing the stent 2 is left free in the bladder and can be recovered if need be.

If the thread is pulled along by the urine flow, the part above the sphincter does not require clinical measures. In particular, there is no incontinence.

Furthermore, the inventors noticed that the transition between the kidney end part 200 and the bladder end part 210 must be gradual to avoid a sudden change in the diameter of the stent catches in the bends of the ureter U.

In this regard, the stent further comprises an intermediate portion 220, extending between the kidney end part 200 and the bladder end part 210.

According to the first embodiment, in FIGS. 2a to 2d and 8a and 8b, this intermediate portion is intended to be positioned in the ureter U when the stent 2 is in place.

According to the alternative embodiment represented in FIGS. 3a and 3b, the intermediate portion is intended to be positioned in the kidney R when the stent 2 is in place, so that only one or two threads are in the ureter.

This intermediate portion 220 is tubular, i.e. it comprises a wall 221 of annular section and further comprises an internal channel 222 into a guide can be slid for placing the stent, and in which a fluid can circulate once the stent is in place.

The channel 222 is located in the extension of the channel 202 of the kidney end part in such a way as to allow the fluid communication between the two.

With reference to FIGS. 2a and 2b, the intermediate portion 220 has a variable external diameter $D_{220}$, decreasing toward the bladder end part 210 so that the minimum external diameter of the intermediate portion 220 at the connection with the thread is substantially equal to the diameter $D_{210}$ of the thread of the bladder end part 210. The term "substantially" means that the minimum diameter of the intermediate portion 220 must not exceed twice the diameter of the thread, or the cumulative section of the threads if there are several of them, and in all cases must be strictly less than 1 mm, and preferably less than 0.5 mm, the connection between the intermediate portion and the thread(s) then being as smooth as possible (for example chamfered) to avoid any serrated bumps liable to cause pain. This makes it possible to provide a gentle and regular transition between the two end diameters of the stent and to confer greater flexibility on the stent so that the latter can adapt to the curvature of the ureter. This reduces pain related to the presence of the stent and facilitates its removal.

Specifically, FIGS. 7a to 7c represent the motion of the stent inside the ureter with the breathing of the person in whom the stent is implanted. The 3 following cases are identified:

In FIG. 7a, a stent of JJ type has a clean break without any intermediate portion 220 providing a transition between the two. If the stent is found at a distance from a curve in the ureter, the movements of this stent do not lead to pain.

On the other hand, with reference to FIG. 7b, if this stent moves in the ureter and reaches a curve, the movements of this stent inside the ureter with breathing causes pain due to the abrupt and rigid end of the stent digging into the ureter wall.

With reference to FIG. 7c, it is observed that the presence of an intermediate portion forming the transition between the thread and the kidney end portion increases the flexibility of the stent and thus eliminates pain in the curves of the ureter during breathing.

In the same way, removal of the stent is facilitated since the intermediate portion gives the stent flexibility, which makes it possible to guide this stent in the ureter during its removal without blocking it.

The maximum external diameter of the intermediate portion 220 is equal to that of the kidney end portion.

Thus, by way of non-limiting example, the intermediate portion has a diameter that decreases evenly from a diameter of about 2.4 mm to a diameter of about 0.15 mm.

The tubular part of the stent 2, i.e. the part of the stent that contains an internal channel, terminates at the end of the intermediate portion 220.

In this regard, the internal channel 222 of the portion 220 opens in the ureter through a hole (not represented) formed in the wall 221, close to the junction with the thread 210 of the bladder end part.

According to a preferred embodiment, represented in FIGS. 6a and 6b, the intermediate portion 220 of the stent is bevelled, so that the intermediate portion comprises a first tubular portion 224, and a second portion 225 terminating the intermediate portion 220, the portion 225 being laterally open, so that the channel 222 opens in the ureter, as second portion is de facto solid, i.e. non-tubular, and extended by the bladder end part 210. This embodiment is advantageous because the bevel shape has a continuity that allows the stent to avoid catching in the ureter.

Furthermore, due to the bevel the portion 225 is very flexible, which further reduces the risk of catching and guides the stent inside the ureteral folds during the breathing movements.

The thread 210 can be formed on the wall of the intermediate portion 220. Alternatively, it can be added to it, for example glued or fastened onto the wall, or else knotted at a hole 223.

Advantageously, the thread 210 emerges from the internal channel 222 of the intermediate portion 220, i.e. it is joined onto the cylindrical wall 221 to form a single part, on an internal surface of the latter, so as not to form an excrescence on the external surface of the wall 221, as schematically illustrated in FIG. 2a.

In the embodiment in FIGS. 3a and 3b, a thread is advantageously added on to the intermediate portion 220 and folded in half, preferably at its middle, to obtain a double thread. This procedure is however also applicable to the embodiment in FIGS. 2a and 2b.

As can be seen in FIG. 3a, the thread passes through a first hole in the wall of said portion 220 at the beveled tip 225 of the latter, and passes again through the wall of the stent in the vicinity of the junction between the intermediate portion 220 and the kidney end part 210, i.e. either at the tubular portion 224, of at the end of the kidney end part 210.

This also increases the strength of the fastening of the bladder end part to the intermediate portion, particularly upon removal of the stent, because the portion of the stent at the beveled tip is fragile and can break.

This also makes it possible to remove the stent without pain, because attaching the thread only at the kidney end part or at its junction with the intermediate portion could lead to the beveled tip curving at the moment the stent is removed, and causing pain by irritating the ureter or the kidney.

Lastly, the thread is advantageously knotted on either side of the wall of the beveled tip 225 to hold it in position.

Alternatively, and preferably, in a similar way to the representation in FIG. 2a, at least one thread 210 can be formed onto the wall of the intermediate portion 220 or be added to the latter, for example glued or fastened, and emerge from the internal channel 222 of the intermediate portion 220 (at the beveled tip 225). This preserves the continuity of the various parts of the stent and avoids incurring inconvenience for the patient.

In general the wall of the stent must be as smooth as possible, and free of bumps (no sudden variation in angle, clean break, or surface roughness) to avoid any irritation of the ureter and any discomfort for the patient.

In FIG. 2b, the junction between the intermediate portion 220 and the bladder end part 210 is very preferably located at a distance from the meatus M of the ureter when the stent 2 is in place, i.e. from the hole of the ureter that opens in the bladder, so that only the thread 210 crosses the meatus and enters the bladder V.

In this regard, the intermediate portion 220 has a length between 0.5 and 12 cm, depending on the position of an obstruction of the ureter—the portion 220 then has a section that decreases evenly over its whole length, preferably in the order of 3 cm. This length makes it possible to provide a gentle transition between the two end portions of the stent.

The combined contribution of the thread(s) and the gentle transition between these threads and the kidney end part 200 thus makes it possible to significantly improve patient comfort.

In the embodiment represented in FIGS. 3a and 3b, the intermediate portion advantageously has a length in the order of 1 cm, allowing only one or two threads to enter the ureter and then the bladder through the meatus M.

Thus, when the stent 2 is in place, the urine is drained from the kidney to the bladder, passing through the internal channel 202 of the kidney end part 222 and the intermediate portion 220, or along the walls of these parts, then by flowing out along the thread 210.

According to a particular embodiment, represented in FIGS. 8a and 8b, the stent, in which all the previous features are repeated, further comprises a ureteral part 240 extending between the kidney end part 200 and the intermediate portion 220.

This ureteral part is tubular, and therefore comprises a cylindrical wall 241 defining an internal channel 242 communicating at one end with that 202 of the kidney end part 200 and at another end with that 222 of the intermediate portion 220 to ensure fluid communication all the way along the stent.

This part 240 has an external diameter $D_{240}$ equal to that of the kidney end part 200, and a length between 10 and 25 cm, and preferably in the order of 20 cm.

On the other hand, this part 240 is reinforced and in particular does not contain any perforating holes, so that the fluid can only flow inside the internal channel 242.

This part is in the ureter when the stent is in place, and makes it possible to make the urine circulate via the internal channel 242 in the event of strong external compression of the ureter. This situation typically appears in cases of a tumor T adjacent to or surrounding the ureter. The absence of perforations makes it possible to avoid the tumor T obstructing the internal channel 242.

The stent 2 is preferably made of a polymer material, preferably polyurethane or silicone. The thread of the bladder end portion can be made of such a material or of polypropylene.

Thus, a stent has been proposed which does not generate any irritation or reflux in patients, and which, contrary to the feared outcome, manages to drain the urine into the bladder.

The placing of such a stent is carried out to re-establish or improve the draining of urine into the ureter, particularly the placing of a stent in accordance with FIGS. 2a and 2b for an obstructive kidney or ureter stone and an obstructive pyeloureteral junction syndrome, and of a stent in accordance with FIGS. 3a and 3b for a preparation of the ureter with a view to putting in a flexible or rigid ureteroscopy sheath or non-obstructive kidney stone before treating the stone (extracorporeal lithotripsy, treatment by ureteroscopy: treatment by nephroscopy), also of a stent in accordance with FIGS. 8a and 8b for an extrinsic tumoral ureteral stenosis or a malignant or benign retroperitoneal fibrosis or an ischaemic ureteral stenosis or a post-radiation ureteral stenosis or ureteral stenosis or intrinsic tumoral pyelic stenosis.

The operation takes place under general or local anaesthetic. The kidney end part 200 of the stent is placed in the kidney via an endoscope and under a brightness amplifier. A plunger of about 50 cm is necessary to be able to push this part into the kidney. To palliate the lack of length of the plungers conventionally used to push in JJ stents (as the tubular portion of the stent 2 is shorter), one may for example use an ureteral stent such as the Open-End Flexi-Tip Ureteral Catheter, 5F (or 1.67 mm)/70 cm, from Cook Medical.

The thread(s) of the bladder end part are left in the bladder, taking care not to push them into the ureter with the rest of the stent.

For removal, the stent can be removed under local anaesthesia using a fibroscope and a forceps by pulling on a thread. A thread does not break upon removal of the stent, but the ablation can be delicate in the absence of a suitable item of gripping equipment. For example, a biopsy forceps may advantageously be used, such as the model Karl Storz—Endoskope, Biopsy Forceps, double action jaws, 7F (or 2.33 mm), length 40 cm, 27175A.

The invention claimed is:

1. An endo-ureteral stent (2), comprising a kidney end part (200) and a bladder end part (210), the kidney end part (200) being tubular and coiled,
   wherein the bladder end part (210) includes at least one thread, and in that the stent further comprises a tubular intermediate portion (220) extending between the kidney end part and the bladder end part, said portion having an external diameter ($D_{220}$) decreasing toward the bladder end part, and the minimum external diameter of said portion (220), at the point of connection with the thread of the bladder end part (210), is substantially equal to the diameter of the thread, said intermediate portion (220) having a length between 0.5 cm and 12 cm, and
   wherein the at least one thread is of circular section, each thread having a diameter ($D_{210}$) of less than 0.15 mm.

2. The endo-ureteral stent (2) according to claim 1, wherein the bladder end part (210) includes a single thread.

3. The endo-ureteral stent (2) according to claim 1, wherein the intermediate portion (220) has a length of 3 cm.

4. The endo-ureteral stent (2) according to claim 1, wherein the diameter of the intermediate portion (220) decreases evenly over the whole length of said portion.

5. The endo-ureteral stent (2) according to claim 1, wherein the intermediate portion (220) is beveled.

6. The endo-ureteral stent (2) according to claim 5, wherein the beveled intermediate portion (220) comprises a tubular portion (224) and a solid portion (225) ending said portion (220), the bladder end part (210) comprising a thread crossing the wall of the solid portion (225) and the wall of the tubular portion (224) or of the kidney end part (200).

7. The endo-ureteral stent (2) according to claim 2, wherein the intermediate portion (220) comprises a tubular portion (224) and a solid portion (225) extended by the bladder end portion (210), the thread of the bladder end portion (210) being formed onto a wall of the intermediate portion (220).

8. The endo-ureteral stent (2) according to claim 1, wherein the bladder end part (210) has a length greater than or equal to 2 cm.

9. The endo-ureteral stent (2) according to claim 1, wherein the kidney end part (200) and the intermediate portion (220) each comprise a plurality of through perforations (203, 223).

10. An endo-ureteral stent (2) comprising a kidney end part (200) and a bladder end part (210), the kidney end part (200) being tubular and coiled,
wherein the bladder end part (210) includes at least one thread, and in that the stent further comprises a tubular intermediate portion (220) extending between the kidney end part and the bladder end part, said portion having an external diameter ($D_{220}$) decreasing toward the bladder end part, and the minimum external diameter of said portion (220), at the point of connection with the thread of the bladder end part (210), is substantially equal to the diameter of the thread, said intermediate portion (220) having a length between 0.5 cm and 12 cm,
wherein the endo-ureteral stent further comprises a tubular ureteral part (240) arranged between the kidney end part (200) and the intermediate portion (220), said ureteral part (240) having an external diameter ($D_{240}$) equal to that of the kidney end part (200) and being unperforated.

11. The endo-ureteral stent (2) according to claim 10, wherein the tubular ureteral part (240) has a length between 10 and 25 cm.

12. A method for treating a urological disorder by implanting an endo-ureteral stent, wherein the urological disorder comprises an obstruction within the ureter, the method comprising:
implanting an endo-ureteral stent within a ureter of a subject, the endo-ureteral stent comprising a kidney end portion, a bladder end portion, and an intermediate portion extending between the kidney end portion and the bladder end portion, the intermediate portion having an external diameter decreasing toward the bladder end portion, and the bladder end portion having at least one thread extending from the intermediate portion, the implanting comprising positioning the thread of the endo-ureteral stent downstream the obstruction, and
treating the urological disorder by dilating the ureter with the endo-ureteral stent.

13. The method according to claim 12, wherein implanting the stent comprises positioning the kidney end portion in a kidney of the subject and at least one thread in the ureter so that said at least one thread causes dilating of the ureter.

14. The method according to claim 12, wherein implanting the stent comprises positioning the kidney end portion in the kidney and the intermediate portion in the ureter so that said at least one thread extends from the ureter into the bladder.

15. The method according to claim 12, wherein implanting comprises positioning the intermediate portion in the kidney such that the at least one thread extends from the kidney into the ureter.

16. The method according to claim 12, wherein the urological disorder comprises kidney or ureteral stones, and dilating the ureter comprises dilating the ureter with the at least one thread to a diameter that allows the stones, or fragments thereof, to be evacuated naturally during urination.

17. The method according to claim 12, wherein the urological disorder comprises one of kidney stones, ureter stones, obstructive syndrome of the pyeloureteral junction, extrinsic ureteral tumor stenosis, malignant retroperitoneal fibrosis, benign retroperitoneal fibrosis, ischaemic ureteral stenosis, post-radiation ureteral stenosis or intrinsic tumoral ureteral or pyelic stenosis.

18. A method of treating a urological disorder by implanting an endo-ureteral stent, the method comprising:
implanting an endo-ureteral stent within a ureter of a subject, the endo-ureteral stent having a thread portion dimensioned to dilate the ureter,
waiting for a time period of at least ten days to allow dilation of the ureter due to the presence of the thread portion of the endo-ureteral stent, and
treating the urological disorder in the dilated ureter.

19. The method according to claim 18, wherein thread portion comprises a circular section having a diameter of less than 0.15 mm.

20. The method according to claim 18, wherein the endo-ureteral stent further comprises a tubular portion having a decreasing diameter toward one end, and wherein the thread portion extends from the one end of the tubular portion, and implanting comprises positioning the tubular portion in a kidney of the subject and the thread portion in the ureter.

21. The method according to claim 20, wherein the tubular portion comprises a coiled portion at an end opposite the one end, and the coiled portion and the one end have holes, and a ureteral portion extending between the coiled portion and the one end is devoid of holes, and implanting comprises positioning the ureteral portion and the thread portion in the ureter.

22. The method according to claim 18, wherein the urological disorder comprises kidney stones or ureteral stones, and treating comprises evacuating the stones, or fragments of the stones, from the kidney or ureter while the endo-ureteral stent remains implanted in the ureter.

23. The method according to claim 18, wherein the urological disorder comprises one of kidney stones, ureter stones or obstructive syndrome of the pyeloureteral junction and implanting comprises positioning the tubular portion of the endo-ureteral stent in a kidney of the subject and the thread portion in the ureter.

24. The method according to claim 18, wherein the urological disorder comprises one of an extrinsic ureteral tumor stenosis, malignant retroperitoneal fibrosis, benign retroperitoneal fibrosis, ischaemic ureteral stenosis, post-radiation ureteral stenosis or intrinsic tumoral ureteral or pyelic stenosis.

25. The endo-ureteral stent according to claim 1, wherein the bladder end part has a length between 5 and 30 cm.

* * * * *